(12) United States Patent
English et al.

(10) Patent No.: US 10,436,677 B2
(45) Date of Patent: Oct. 8, 2019

(54) SAMPLE CONDITIONING

(71) Applicant: BP Corporation North America Inc., Houston, TX (US)

(72) Inventors: Jason English, Aurora, IL (US); Craig Hackett, Aurora, IL (US)

(73) Assignee: BP Corporation North America Inc., Houston, TX (US)

( * ) Notice: Subject to any disclaimer, the term of this patent is extended or adjusted under 35 U.S.C. 154(b) by 241 days.

(21) Appl. No.: 15/628,874

(22) Filed: Jun. 21, 2017

(65) Prior Publication Data

US 2018/0017469 A1    Jan. 18, 2018

Related U.S. Application Data

(60) Provisional application No. 62/362,150, filed on Jul. 14, 2016.

(51) Int. Cl.
| | |
|---|---|
| *G01N 1/20* | (2006.01) |
| *G01N 33/28* | (2006.01) |
| *G01N 1/44* | (2006.01) |
| *G01N 1/34* | (2006.01) |
| *G01N 1/40* | (2006.01) |

(52) U.S. Cl.
CPC ............ *G01N 1/20* (2013.01); *G01N 1/2035* (2013.01); *G01N 1/44* (2013.01); *G01N 33/2823* (2013.01); *G01N 33/2829* (2013.01); *G01N 33/2835* (2013.01); *G01N 1/34* (2013.01); *G01N 1/4022* (2013.01); *G01N 2001/205* (2013.01); *G01N 2001/2064* (2013.01)

(58) Field of Classification Search
CPC .......... G01N 1/20; G01N 1/2035; G01N 1/34; G01N 1/44; G01N 2001/205; G01N 33/2829; G01N 33/2835
See application file for complete search history.

(56) References Cited

U.S. PATENT DOCUMENTS

| | | |
|---|---|---|
| 2,571,470 A | 10/1951 | Milligan |
| 8,497,683 B2 | 7/2013 | Trygstad et al. |
| 2014/0020453 A1 | 1/2014 | Estrada et al. |
| 2016/0047792 A1 | 2/2016 | Ghosh et al. |

FOREIGN PATENT DOCUMENTS

| | | | | |
|---|---|---|---|---|
| GB | 2 170 909 | | 8/1986 | |
| GB | 2292607 A | * | 2/1996 | ............ G01N 17/008 |

* cited by examiner

*Primary Examiner* — Paul M. West
(74) *Attorney, Agent, or Firm* — Kalim S. Fuzail

(57) ABSTRACT

A process for analyzing a hydrocarbon stream comprises: withdrawing a hydrocarbon sample from a hydrocarbon stream; passing the hydrocarbon sample to an analysis device at a target temperature of greater than 120° C. and a target flow rate of greater than 20 liters per minute; and returning the hydrocarbon sample to the hydrocarbon stream. The process may be used for the on-line analysis of crude oil, in order to optimize a refinery operation.

5 Claims, 2 Drawing Sheets

SAMPLE CONDITIONING

CROSS-REFERENCE TO RELATED APPLICATIONS

This application claims priority, under 35 U.S.C. § 119(e), of Provisional Application No. 62/362,150, filed Jul. 14, 2016, incorporated herein by this reference.

FIELD OF THE INVENTION

The present invention relates to a process for analysing a hydrocarbon stream. In particular, the present invention relates to a process for the on-line analysis of a hydrocarbon stream, e.g. a crude oil stream, in which a hydrocarbon sample is passed around a sample loop. The process may be used as part of a process for controlling, e.g. optimising, a large-scale refinery operation such as a desalting operation.

BACKGROUND OF THE INVENTION

When crude oil is extracted from a reservoir, it contains water and salts. At the high temperatures that may be encountered in a refinery during crude oil processing, the water can hydrolyse the salts to form corrosive acids. Chloride salts are typically found in crude oil and pose a particular problem, since they can form hydrochloric acid. Bromide salts can also be found, and they can form hydrobromic acid.

Over time, corrosive acids can cause significant damage to refinery equipment. Damage is commonly observed in the lines that transport crude oil from one area of a refinery to another. Considerable time and cost may be involved in replacing damaged refinery equipment. In some cases, for instance where a bypass pipe has not been provided, processing of the crude oil will need to be stopped entirely in order for the refinery equipment to be replaced.

It is therefore desirable for salts to be removed from hydrocarbon fluids such as crude oil before refinery processing. To solve this problem, crude oils are passed to a desalter before they are processed in a refinery.

Crude oils are typically mixed with wash water before they are passed to the desalter. Once introduced into the desalter, a desalted crude oil phase and an aqueous phase form. The aqueous phase contains water (that which was present in the extracted crude oil, as well as water that has been added to the hydrocarbon stream during processing, such as wash water) and salt. A rag layer separates the two phases. The rag layer is a mixture of the aqueous phase and the desalted crude oil phase.

A desalted crude oil stream and an aqueous stream are withdrawn from the desalter through separate lines. The streams are typically withdrawn at points in the desalter which are a distance from the rag layer so as to minimise the presence of any aqueous components in the desalted crude oil stream and vice versa.

Methods are known for optimising desalting processes. For instance, demulsifiers are often added to minimise the rag layer and encourage the formation of separate hydrocarbon and aqueous phases. The application of an electrostatic field to the desalting unit may also be used to encourage the formation of separate phases.

However, the optimal conditions for operating a desalting process, and indeed for optimising other refinery processes, can vary greatly depending on the composition of the crude oil. It is therefore desirable to sample a crude oil before it is passed to a refinery process, such as a desalting process. This enables the refinery process to be optimised based on the particular crude oil that is being used.

Whilst crude oil may be sampled and tested before it is passed to the refinery, sometimes even before purchase, it is preferable to carry out on-line analysis of the crude oil. This analysis is often done using a sample loop in which a sample of crude oil is withdrawn from a process stream, analysed, and return to the process stream.

For example, GB 2170909 discloses a method for the on-line monitoring of crude oil in which a sample is isolated and circulated around a sample loop which includes a heat exchanger and a densitometer.

U.S. Pat. No. 8,497,683 discloses a spectroscopic sample analysis apparatus which includes an actively controlled heat exchanger in serial fluid communication with a spectroscopic analyzer, and a controller communicably coupled to the heat exchanger. The apparatus may be used to measure properties of the samples by spectroscopic methods, such as nuclear magnetic resonance, infrared, near infrared and Raman spectroscopy.

However, existing methods for the on-line sampling of crude oil suffer from a number of drawbacks. In particular, fouling of the sample loop can occur over time, e.g. around the analysis device, thereby reducing the accuracy of the crude oil analysis. This fouling has previously been thought to be caused by inorganic compounds. To protect the analysis device from inorganic solids, the crude oil is often passed through a filter before it is passed to the analysis device. However, in severe cases of fouling, filters in the sample loop may become plugged, preventing any analysis at all. As a consequence, optimisation of the refinery process to which the crude oil is passed may be compromised.

Accordingly, there is a need for an improved method for the on-line analysis of a refinery feedstock, such as a crude oil. There is also a need for an improved method for controlling a refinery process, such as a desalting process.

SUMMARY OF THE INVENTION

It has now surprisingly been found that fouling of a sample loop may be caused by waxes that are present in hydrocarbon fluids such as crude oils. This is in contrast to the previously held belief that it is the inorganic compounds that are present in crude oil, such as iron sulfide, that are principally responsible for fouling. It has further been found that the deposition of waxes may be prevented by conditioning the hydrocarbon fluid so that it is passed around at least part of the sample loop, e.g. those areas most prone to fouling, at a temperature of greater than 120° C. and a flow rate of greater than 20 liters per minute.

Accordingly, the present invention provides a process for analysing a hydrocarbon stream, said process comprising:

withdrawing a hydrocarbon sample from a hydrocarbon stream;

passing the hydrocarbon sample to an analysis device at a target temperature of greater than 120° C. and a target flow rate of greater than 20 liters per minute; and returning the hydrocarbon sample to the hydrocarbon stream.

Also provided is a process for controlling a refinery operation, said process comprising:

analysing a hydrocarbon stream which is a feedstock for, or a product stream from, the refinery operation using the process disclosed herein; and based on the analysis, modifying or maintaining the conditions under which the hydrocarbon stream is processed in the refinery operation.

DETAILED DESCRIPTION OF THE INVENTION

Figure 1:
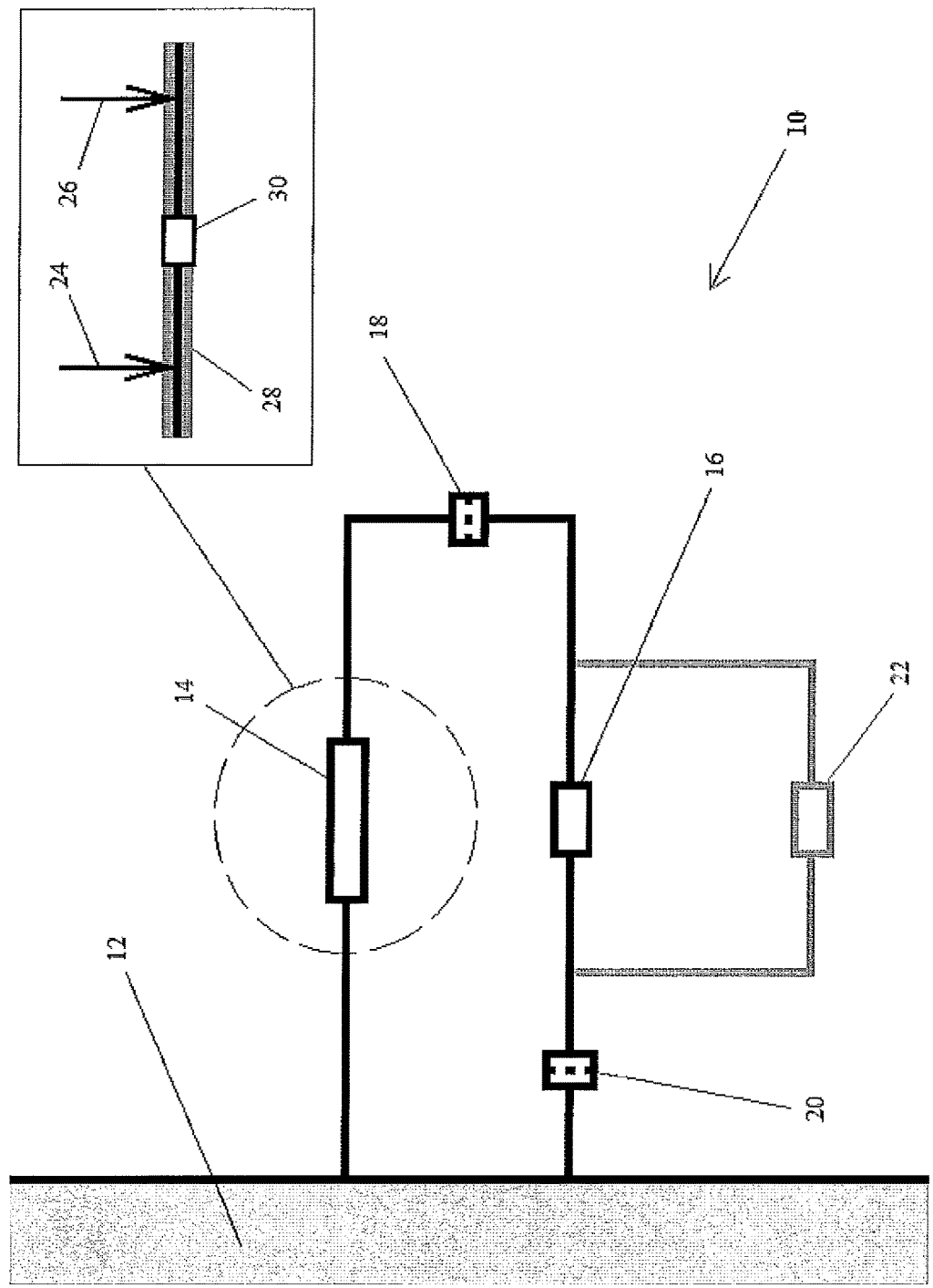
FIG. 1 is a schematic diagram of a sample loop which may be used in accordance with the present invention.

The process of the present invention involves withdrawing a hydrocarbon sample from a hydrocarbon stream, analysing the sample and returning the hydrocarbon sample to the hydrocarbon stream. Thus, the process of the present invention involves passing a hydrocarbon sample around a sample loop. The present invention involves conditioning the hydrocarbon sample so that it is passed to the analysis device at an optimal temperature and flow for reducing fouling.

Accordingly, the process disclosed herein may be used to reduce fouling, e.g. caused by waxes (e.g. alone or in combination with asphaltenes and/or inorganic solids such as iron sulfide), in a hydrocarbon sample loop.

Withdrawing a Hydrocarbon Sample from a Hydrocarbon Stream

The process of the present invention includes the step of withdrawing a hydrocarbon sample from a hydrocarbon stream. It will be appreciated that the hydrocarbon sample will generally be in the form of a sub-stream. Generally, less than 10%, preferably less than 5%, and more preferably less than 1% by volume of the hydrocarbon stream will be withdrawn as the hydrocarbon sample.

The hydrocarbon stream preferably comprises waxes in an amount of greater than 0.1%, more preferably greater than 0.5%, and still more preferably greater than 1% by weight of hydrocarbon stream. The hydrocarbon stream will generally comprise waxes in an amount of less than 25% by weight of hydrocarbon stream. The wax content of the hydrocarbon stream may be measured according to UOP 46-64 or ASTM D2500, and preferably according to ASTM D2500-16. NMR methods may also be used to monitor wax content.

The hydrocarbon stream preferably comprises asphaltenes in an amount of greater than 0.1%, more preferably greater than 2%, and still more preferably greater than 5%, by weight of hydrocarbon stream. The asphaltene content of the hydrocarbon stream may be measured according to ASTM D6560-12. In addition to the waxes that are present in the hydrocarbon stream, asphaltenes may contribute to fouling of the sample loop.

The hydrocarbon stream may also comprise inorganic compounds. In preferred embodiments, the hydrocarbon stream comprises iron sulphide, though the hydrocarbon stream may also comprise clays and calcium carbonates. Inorganic compounds may also contribute to fouling in the sample loop.

The hydrocarbon stream is preferably a crude oil stream. In these embodiments, the sample withdrawn from the hydrocarbon stream will be a crude oil sample. Since crude oil contains heavy components, such as waxes and asphaltenes, as well as inorganic components, such as iron sulfide, it is prone to fouling when passed through a sample loop. Heavier crude oils, i.e. those having a higher content of asphaltenes and waxes, are particularly prone to fouling.

The crude oil stream may be a crude oil stream that is being passed through a production pipeline, a transportation pipeline or a processing pipeline. Preferably the crude oil stream is being passed through a processing pipeline, i.e. it forms part of a refinery apparatus.

In some embodiments, the crude oil may be a raw crude oil (also known as a dead oil, or a stock tank oil). Raw crude oil may be obtained by bringing crude oil from a subterranean formation (i.e. a live oil) to atmospheric conditions, for instance of 20° C. and 100 kPa. Gases that are dissolved in the live oil under subterranean conditions are removed during this process. It will be appreciated that the raw crude oil is used at non-atmospheric conditions during the processes disclosed herein.

Preferably, a sample of the raw crude oil is withdrawn from the crude oil stream before wash water is added thereto, e.g. wash water that may be used in a desalting process.

The raw crude oil is preferably sampled after the crude oil stream has been subjected to heating, e.g. in a preheat train. This reduces the energy input that is required to maintain the temperature of the crude oil sample in the sample loop.

In other embodiments, the crude oil stream may be a desalted crude oil stream. Desalted crude oil streams will generally be at a higher temperature than raw crude oil streams, and so less energy input may be required in the sample loop.

The hydrocarbon sample may be withdrawn from the hydrocarbon stream continuously. However, it is generally preferred for the hydrocarbon sample to be withdrawn from the hydrocarbon stream intermittently. Valves may be used to control the withdrawal of the hydrocarbon sample from the hydrocarbon stream.

Passing the Hydrocarbon Sample to an Analysis Device

The hydrocarbon sample is passed to an analysis device at a target temperature of greater than 120° C. and a target flow rate of greater than 20 liters per minute. As mentioned above, these conditions are believed to minimise fouling and plugging around the analysis device.

The hydrocarbon sample is passed to the analysis device at a target flow rate of greater than 20 liters per minute. Preferably, the hydrocarbon sample is passed to the analysis device at a target flow rate of greater than 25 liters per minute, and more preferably greater than 30 liters per minute. By keeping the sample flowing at a fast rate, fouling of the sample loop with waxes is avoided. The hydrocarbon sample may be passed to the analysis device at a target flow rate of less than 90 liters per minute, preferably less than 75 liters per minute, and more preferably less than 60 liters per minute. For example, the hydrocarbon sample may be passed to the analysis device at a target flow rate of from 35 to 40 liters per minute.

The hydrocarbon sample may be passed to the analysis device at a target velocity of greater than 0.5 m/s, preferably greater than 1 m/s, and more preferably greater than 2 m/s. By maintaining the sample at a relatively high target velocity, the waxes are prevented from plugging the sample loop. The hydrocarbon sample is preferably passed to the analysis device at a target velocity of less than 6 m/s, and more preferably less than 5 m/s, since higher velocities may not be compatible with the analysis device.

The flow rate of the hydrocarbon sample may be achieved by conventional means, such as by using one or more pumps. However, the flow rate is preferably controlled using piping of an appropriate size, shape and length. The flow rate may also be controlled through back pressure control, the use of orifice restrictions, and the use of by-passes. In preferred embodiments, the flow rate of the sample is monitored (and, where necessary, controlled) to ensure that the target flow rate has been achieved. The velocity of the hydrocarbon sample may also be achieved, controlled and monitored in the same way, e.g. to ensure that the target velocity has been reached.

Preferably, the piping through which the hydrocarbon sample is passed in the sample loop has a length of less than 50 m, preferably less than 40 m, and more preferably less than 30 m. Preferably the piping has a diameter of from 0.5 to 2 cm, and more preferably from 0.8 to 1.3 cm. The piping is preferably stainless steel tubing.

The hydrocarbon sample is passed to the analysis device at a target temperature of greater than 120° C. Preferably, the hydrocarbon sample is passed to the analysis device at a target temperature of greater than 130° C., and more preferably greater than 135° C. Whilst an increase in temperature reduces the deposition of waxes, higher temperatures may reduce the viscosity of the sample causing deposition of inorganic solids in the sample loop. Accordingly, the hydrocarbon sample is preferably passed to the analysis device at a target temperature of less than 190° C., more preferably less than 180° C., and still more preferably less than 175° C. For example, the hydrocarbon sample may be passed to the analysis device at a target temperature of from 140 to 170° C. It is surprising that these temperatures are sufficient to reduce fouling of waxes, whilst still minimizing fouling caused by inorganic solids.

The target temperature may be achieved by heating the hydrocarbon sample. Suitable methods for heating the hydrocarbon sample may involve steam cool heaters, electric heat tracing, steam tracing, electric coil heaters and combinations thereof.

Insulation may also be used to minimise heat loss from the hydrocarbon sample. For instance, cladding may be used around the piping through which the hydrocarbon sample is passed in the sample loop.

In preferred embodiments, the process of the present invention involves monitoring the temperature of the hydrocarbon sample and, if the temperature of the hydrocarbon sample falls below the target temperature, heating the hydrocarbon sample. Thus, a temperature detection device may be used which provides feedback to a heating device.

The temperature detection and the heating device are preferably positioned between the point at which the hydrocarbon sample is withdrawn from the hydrocarbon stream and the analysis device. The heating device may be positioned between the point at which the hydrocarbon sample is withdrawn from the hydrocarbon stream and the temperature detection device, or it may be positioned between the temperature detection device and the analysis device. In some embodiments, a heating device will be positioned between the point at which the hydrocarbon sample is withdrawn from the hydrocarbon stream and the temperature detection device, and between the temperature detection device and the analysis device. In embodiments, a plurality of temperature detection devices and a plurality of heating devices are positioned between the point at which the hydrocarbon sample is withdrawn from the hydrocarbon stream and the analysis device.

The input of heat required to achieve the target temperature will be directly dependent on the original sample temperature. Raw crude oil will generally require much more heat input than desalted crude, particularly if it is withdrawn from a crude oil stream before the preheat train.

Typically, the temperature of raw crude oil on withdrawal from the crude oil stream will be around 90° C. or greater, whereas the temperature of desalted crude oil will be around 110° C. or greater.

The hydrocarbon sample will generally be passed to the analysis device (and preferably maintained throughout the sample loop) below its flash point. The process of the present invention may therefore comprise pressurising the hydrocarbon sample before it is passed to the analysis device. This prevents the more volatile components in the hydrocarbon sample from flashing off when heat is applied. The hydrocarbon sample may be passed to the analysis device at a target pressure of from 200 to 1500 KPa, preferably from 250 to 1250 KPa, and more preferably from 400 to 1000 KPa.

The analysis device may be used to measure a chemical or physical property of the hydrocarbon stream, or combinations thereof.

Suitable properties may be selected from chlorine content, sulfur content, water content, density, viscosity and content of metal elements (e.g. calcium, iron, nickel, and vanadium content).

Suitable analysis devices include x-ray diffraction (XRD) devices (e.g. to measure the chlorine content, sulfur content and content of metal elements), microwave detection devices (e.g. to measure water content), and a Coriolis flow meter or a densitometer (e.g. to measure density and viscosity).

Preferably, the analysis device measures the chlorine content of the hydrocarbon sample. Examples of suitable XRD devices for measuring the chlorine content of the hydrocarbon sample include Clora devices provided by X-Ray Optical Systems (known as XOS). This embodiment is particularly preferred where the hydrocarbon stream is a feedstock to, or a product stream from, a desalter, since it enables the conditions in the desalter to be modified or maintained in order to optimise the desalting process.

The hydrocarbon sample may be passed to a single analysis device, or it may be passed to at least two analysis devices. In some embodiments, the hydrocarbon sample may be passed to at least two analysis devices in series. In other embodiments, the hydrocarbon sample may be separated into sub-samples, with each of the sub-samples passed to an analysis device in parallel.

The hydrocarbon sample is preferably filtered before it is passed to the analysis device. This enables solids to be removed from the hydrocarbon sample before it is analysed.

The filter may have a mesh size of from 25 to 2000 μm, preferably from 50 to 1000 μm, and more preferably from 80 to 500 μm.

To minimise fouling of the filter, the hydrocarbon sample is preferably filtered at the target temperature and the target flow rate. The hydrocarbon sample is preferably also maintained at the target temperature and the target flow rate between the filter and the analysis device. The hydrocarbon sample is also preferably filtered, and preferably maintained between the filter and the analysis device, at the target velocity and/or target pressure.

Whilst maintaining the hydrocarbon sample at the target temperature and the target flow rate (and other optional target conditions, such as target velocity and target pressure) reduces the degree of fouling that takes place in the sample loop, some fouling may still occur. Accordingly, in preferred embodiments, any filters that are used are subjected to backwashing, i.e. a process in which a backwash medium is passed through a filter in the opposite direction to which the hydrocarbon sample is passed through the filter.

The backwash medium is preferably maintained at the target temperature of the hydrocarbon sample.

The backwash medium may be any suitable fluid, such as a hydrocarbon fluid (e.g. crude oil or diesel) or nitrogen. The backwash Medium is preferably the same fluid as that of the hydrocarbon stream and hydrocarbon sample. In these embodiments, the backwash medium may be withdrawn from the hydrocarbon stream.

Returning the Hydrocarbon Sample to the Hydrocarbon Stream

Once the hydrocarbon sample has been passed to, and analysed using, the analysis device, it is returned to the hydrocarbon stream.

The hydrocarbon sample may be filtered after it has been passed to the analysis device but before it is returned to the hydrocarbon stream. The filter may have a mesh size of from 25 to 2000 µm, preferably from 50 to 1000 µm, and more preferably from 75 to 500 µm.

As with the filter before the analysis device, the hydrocarbon sample is preferably filtered at the target temperature and the target flow rate, and more preferably maintained at the target temperature and the target flow rate between the analysis device and the filter. The hydrocarbon sample is also preferably maintained between the analysis device and the filter, and preferably filtered, at the target velocity and/or target pressure.

In embodiments where the hydrocarbon sample has been pressurised, the hydrocarbon sample may be depressurised before it is returned to the hydrocarbon stream. Accordingly, in some embodiments, the process of the present invention involves pressuring the hydrocarbon sample, passing the pressurised hydrocarbon sample to the analysis device, depressurising the hydrocarbon sample, and returning the depressurised hydrocarbon sample to the hydrocarbon stream.

Alternatively, e.g. where the crude sample is raw crude oil, it may be returned to the raw crude oil stream downstream of the mix valve in a two-stage desalter without being depressurised.

Where the hydrocarbon sample is withdrawn from the hydrocarbon stream intermittently, valves may be used to control the return of the hydrocarbon sample to the hydrocarbon stream.

Use of a Sample Loop for Adjusting Hydrocarbon Stream Processing Conditions

The process of the present invention may be used as part of a process for controlling a refinery operation. According to the process, a hydrocarbon stream which is a feedstock for, or a product stream from, the refinery operation is analysed using a process disclosed herein. Based on the analysis, the conditions under which the hydrocarbon stream is processed in the refinery operation may be modified or maintained.

In preferred embodiments, the refinery operation is a desalting operation that is carried out in a desalting unit. In these embodiments, crude oil is preferably used as the feedstock for, or the product stream from, the desalting operation, and the chlorine content of the feedstock is preferably measured.

Any conventional desalting unit may be used in the invention. A desalting unit will typically have an inlet, a hydrocarbon outlet and an aqueous outlet. In the process of the invention, the hydrocarbon stream, water and salt are introduced into the desalter via the inlet. A hydrocarbon phase is removed from the desalter via the hydrocarbon outlet. An aqueous phase is removed from the desalter via the aqueous outlet.

The conditions under which the desalter is operated may be modified or maintained based on the chlorine content of the crude oil. Preferably, the conditions are modified. For instance, the following conditions of the desalting operation may be modified: the amount of wash water that is added to the feedstock, the amount or type of additives (such as demulsifiers) that are added to the feedstock, the degree of mixing that the feedstock and wash water and/or additives are subjected to before introduction into the desalting unit, the temperature in the desalting unit, the pressure in the desalting unit, and the electrostatic field that is applied in the desalting unit.

The process for controlling the desalting operation may be used to optimise the desalting operation. In some instances, the process of the present invention optimises desalting operation by increasing the proportion of salt that is removed from the hydrocarbon stream during desalting. An optimised desalting operation preferably reduces the total inorganic chloride concentration to less than 5 ppm. Where the desalting operation is a two stage process, the total inorganic chloride concentration may be reduced to less than 2 ppm. The desalting operation may also be optimised by improvements in efficiency. Improvements in efficiency include increases in throughput, decreases in the energy used to carry out the desalting process and decreases in the cost of the apparatus used to carry out the desalting process.

The process of the present invention may also be used optimise refinery processes that are found downstream of a desalter and which benefit from an improvement in the desalting operation. For example, the processes described herein may be to reduce furnace fouling, and to increase the lifetime of catalysts that are found downstream of a desalter in a refinery, e.g. catalysts found in process units such as a fluid catalytic cracking (FCC) unit.

The invention will now be described with reference to the accompanying non-limiting figures and examples.

FIG. 1 is a diagram of a sample loop (10) for use in accordance with the process of the present invention. The sample loop comprises a sample conditioning unit (14), an analysis device (16) and two filters (18, 20). The sample conditioning unit (14) comprises sensors (24, 26) and a heating device (30). A further analysis device (22) is shown as part of an optional sub-loop.

Though only shown in the inset of FIG. 1, the tubing through which the hydrocarbon sample is passed in the sample loop (10) is covered with insulative cladding (28). This helps to maintain the hydrocarbon sample at the target temperature.

In use, a hydrocarbon sample is withdrawn from hydrocarbon stream (12) and passed to a sample conditioning unit (14). The sensors (24, 26) in the sample conditioning unit (14) test the temperature of the hydrocarbon sample, and a heating device (30) supplies additional heat to the hydrocarbon sample, if necessary. Sensor (24) is used to determine whether additional heat should be added by heating device (30), whilst sensor (26) is used to check that sufficient heat has been added.

The hydrocarbon sample is then passed to filter (18) at the target temperature and flow rate (though not shown, the sample loop of FIG. 1 may comprise means, e.g. pumps, for maintaining the hydrocarbon sample at the target flow rate). The filter (18) removes any larger solid particles, such as any inorganic solids that may be present in the hydrocarbon sample.

The hydrocarbon sample is maintained at the target temperature and target flow rate as it is passed to the analysis device (16). The sample loop shown in FIG. 1 comprises an optional sub-loop on which a further analysis device (22) is present. Where the sub-loop is used, the hydrocarbon sample is separated into sub-samples and passed to the analysis devices (16, 22) in parallel.

The hydrocarbon sample is then passed to filter (20) which removes any solids that may have formed in the sample loop (10) from the hydrocarbon sample before it is passed back to hydrocarbon stream (12).

EXAMPLES

Example 1: Evidence that Waxes are Responsible for Fouling

Fresh filters (100 μm and 120 μm) were fitted before and after an analysis device in a crude oil sample loop. A crude oil sample was originally passed at a flow rate of greater than 20 liters/minute. The crude oil sample was not subjected to any heating, and no insulation was provided to maintain its temperature through the sample loop. As fouling occurred on the filters, the flow rate of the crude oil sample around the sample loop slowed. As any heat in the sample loop was provided only by the crude oil, the reduced flow rate also led to a reduction in the temperature in the sample loop. The sample loop failed due to plugging of the filters within a couple of weeks.

Microscopic examination of the filters unexpectedly showed that the majority of the fouling was caused by waxes, with minimal inorganic fouling. Although it is known that crude oils contain wax, it was surprising that a sufficient amount of wax had agglomerated in particulate form to lead to plugging of the filters.

Figure 2:
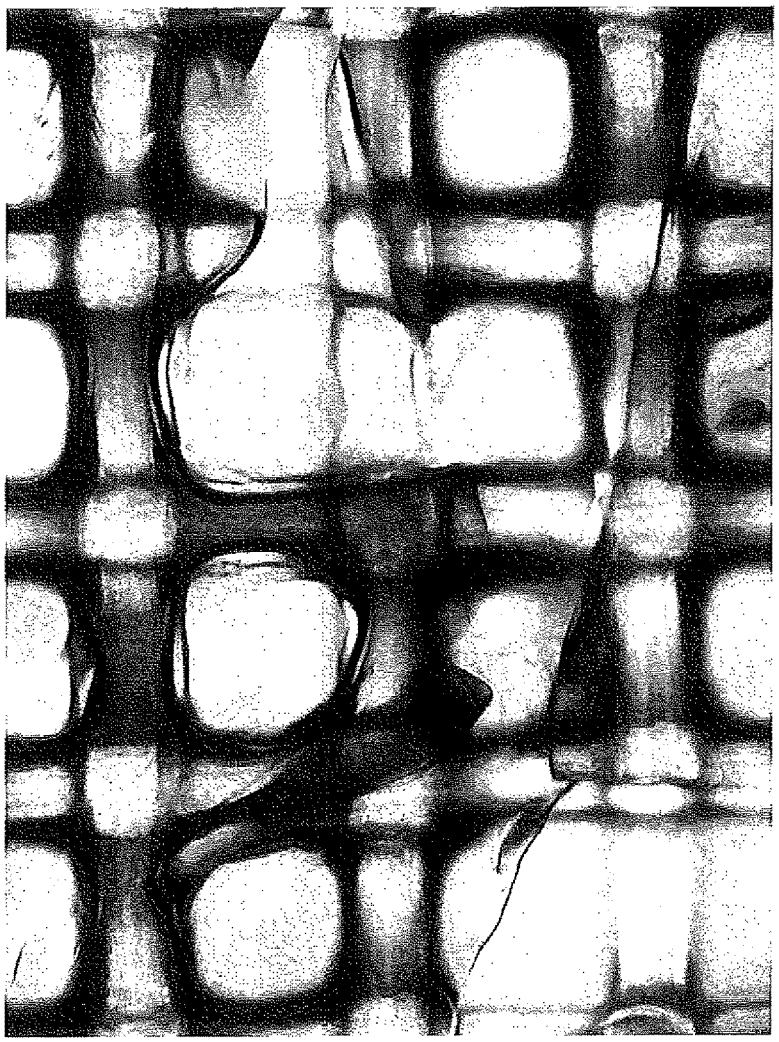
FIG. 2 shows an image of wax fouling on a 100 μm filter, caused by contacting 2000 mL of crude oil with the filter at 60° C.

Small-scale tests were also conducted on a 100 μm filter to confirm the nature of the fouling. 2000 mL of crude oil was contacted with the filters at 60° C. FIG. 2 shows an image of a filter after one of the tests. The presence of wax on the filter can clearly be seen from in the image.

Example 2: Investigating Conditions Suitable for Reducing the Build-Up of Wax

Small-scale tests were conducted to investigate the effect of temperature on the fouling of 100 μm and 120 μm filters. 20 mL of crude oil was contacted with the filters at temperatures ranging from 40 to 95° C. For the 100 μm filters, higher degrees of fouling were observed on the tests run at 40° C. and 60° C. than the test run at 95° C., though fouling was exhibited at all temperatures. Higher degrees of fouling were also observed on the tests run at 40° C. and 60° C. than the test run at 95° C. for the 120 μm filters. The tests demonstrate that, at 95° C., fouling is reduced but still present on the filters. Accordingly, higher crude oil conditioning temperatures, such as a temperature of greater than 120° C., are believed to be necessary.

A larger crude oil sample size was used for more accurate testing. 2000 mL of crude oil was contacted with 100 μm filters at 60° C. The filters were then backwashed with diesel and dried at 60° C. and at 95° C. The results of the experiment are shown in the following table:

| Backwash | Weight of solids (g) | Solids removed |
|---|---|---|
| None | 0.0028 | 0% |
| 60° C. diesel | 0.0013 | 53% |
| 95° C. diesel | 0.0004 | 86% |

It can be seen that backwashing removes some, though not all, of the wax deposits, with the higher temperature backwash medium removing a higher proportion of solids. Accordingly, while backwashing may be a useful tool in removing solids, prevention of wax build-up is nonetheless believed to be necessary.

Prevention of wax build-up was proposed by conditioning the hydrocarbon fluid so that it is passed through the filters and analysis device at a temperature of greater than 120° C. and a flow rate of greater than 25 liters per minute.

Example 3: Testing the Sample Conditioning Method

A full-scale desalting operation was conducted. A sample loop was used to withdraw and analyse a sample from a crude oil stream that formed part of the desalting operation. The sample was passed through a filter and to the analysis device at a temperature of greater than 120° C. and a flow rate of greater than 20 liters per minute. Reduced plugging of the filter was observed.

What is claimed is:

1. A process for analysing a hydrocarbon stream, said process comprising:
    withdrawing a hydrocarbon sample from a hydrocarbon stream;
    passing the hydrocarbon sample to an analysis device at a target temperature of greater than 120° C. and a target flow rate of greater than 20 liters per minute; and
    returning the hydrocarbon sample to the hydrocarbon stream; wherein the analysis device is used to measure a chemical property of the hydrocarbon fluid, a physical property of the hydrocarbon fluid, or combinations thereof, and wherein the analysis device measures the chlorine content of the hydrocarbon fluid.

2. A process for analysing a hydrocarbon stream, said process comprising:
    withdrawing a hydrocarbon sample from a hydrocarbon stream;
    passing the hydrocarbon sample to an analysis device at a target temperature of greater than 120° C. and a target flow rate of greater than 20 liters per minute; and
    returning the hydrocarbon sample to the hydrocarbon stream, wherein the hydrocarbon sample is passed through a filter before it is passed to the analysis device.

3. A process for analysing a hydrocarbon stream, said process comprising:
    withdrawing a hydrocarbon sample from a hydrocarbon stream;
    passing the hydrocarbon sample to an analysis device at a target temperature of greater than 120° C. and a target flow rate of greater than 20 liters per minute; and
    returning the hydrocarbon sample to the hydrocarbon stream, wherein the hydrocarbon sample is passed through a filter before it is passed to the analysis device, and wherein the hydrocarbon sample is filtered at the target temperature and the target flow rate.

4. A process for analysing a hydrocarbon stream, said process comprising:
    withdrawing a hydrocarbon sample from a hydrocarbon stream;
    passing the hydrocarbon sample to an analysis device at a target temperature of greater than 120° C. and a target flow rate of greater than 20 liters per minute; and
    returning the hydrocarbon sample to the hydrocarbon stream, wherein the hydrocarbon sample is passed through a filter before it is passed to the analysis device, and wherein the hydrocarbon sample is filtered at the target temperature and the target flow rate, and wherein the filter is backwashed using a backwash medium.

5. A process for analysing a hydrocarbon stream, said process comprising:
   withdrawing a hydrocarbon sample from a hydrocarbon stream;
   passing the hydrocarbon sample to an analysis device at a target temperature of greater than 120° C. and a target flow rate of greater than 20 liters per minute; and
   returning the hydrocarbon sample to the hydrocarbon stream, wherein the hydrocarbon sample is passed through a filter before it is passed to the analysis device, and wherein the hydrocarbon sample is filtered at the target temperature and the target flow rate, and wherein the filter is backwashed using a backwash medium, and wherein the backwash medium is at the target temperature of the hydrocarbon sample.

* * * * *